United States Patent [19]

Sun

[11] Patent Number: 5,488,110
[45] Date of Patent: Jan. 30, 1996

[54] HIGHLY WATER SOLUBLE BIS-NAPHTHALIMIDES USEFUL AS ANTICANCER AGENTS

[75] Inventor: Jung-Hui Sun, Hockessin, Del.

[73] Assignee: The Du Pont Merck Pharmaceutical Company, Wilmington, Del.

[21] Appl. No.: 219,596

[22] Filed: Mar. 29, 1994

Related U.S. Application Data

[63] Continuation-in-part of Ser. No. 805,045, Dec. 11, 1991, abandoned.

[51] Int. Cl.⁶ .................... C07D 221/14; A61K 31/47
[52] U.S. Cl. ................................................ 546/100
[58] Field of Search ............................ 546/100

[56] References Cited

U.S. PATENT DOCUMENTS

| | | | |
|---|---|---|---|
| 4,841,052 | 6/1989 | Harnisch et al. | 546/99 |
| 4,874,863 | 10/1989 | Brana et al. | 546/100 |
| 5,206,249 | 4/1993 | Sun | 546/99 |
| 5,206,250 | 4/1993 | Sun | 546/99 |

FOREIGN PATENT DOCUMENTS

| | | |
|---|---|---|
| 506008 | 9/1992 | European Pat. Off. |
| WO9217453 | 10/1992 | WIPO |
| WO9312092 | 6/1993 | WIPO |

OTHER PUBLICATIONS

Estey, Cancer Treatment Rep 70, p. 1105 (1986).
Martin et al, Cancer Treatment Report 68, 1317 (1984).
Kolata, New York Times Jul. 26, 1994, p. C3.
Dermer, Biotechnology vol. 12, p. 320 (Mar. 1994).
Marsoni, Cancer Treatment Report 71, p. 71 (1987).
Kubota, GANN, 69, pp. 299–309 (Jun. 1978).
Mattern et al. (1988) *Cancer and Metastasis Reviews* 7: 263–284.
Fujita et al. (Abstract No. 2204) (1993) *Proc. Am. Assoc. Cancer Res.*, 34: 370.
Sakamoto et al. (Abstract No. 2222) (1993) *Proc. Am. Assoc. Cancer Res.*, 34: 373.
Goldin and Venditti (1980) Recent Results Cancer Research 76: 176–191.
Winograd, New Drug Development, in *The Nude Mouse in Oncology Research* (Boven and Winograd, eds.), CRC Press, 1991, pp. 309–316.

*Primary Examiner*—Mark L. Berch

[57] ABSTRACT

This invention relates to bis-naphthalimides, including 2,2'-[1,2-ethanediylbis(methylimino-2,1-ethanediyl)]-bis[5-nitro-1H-benz[de]isoquinoline-1,3(2H)-dione], 2-[2-[N-methyl-N-[2-[[2-(5-nitro-1,3-dioxo-1H-benz[de]isoquinoline-2(3H)-yl)ethyl]amino]ethyl]amino]ethyl]-5-nitro-1H-benz[de]isoquinoline-1,3(2H)-dione, 2,2'-[1,2-ethanediylbis(imino-2,1-ethanediyl)]-bis[5-nitro-1H-benz[de]isoquinoline-1,3(2H)-dione], pharmaceutical compositions containing them, and methods of using them to treat solid tumor carcinomas in mammals.

3 Claims, No Drawings

HIGHLY WATER SOLUBLE BIS-NAPHTHALIMIDES USEFUL AS ANTICANCER AGENTS

CROSS-REFERENCE TO EARLIER FILED APPLICATIONS

This application is a continuation-in-part of U.S. patent application Ser. No. 07/805,045, filed Dec. 11, 1991, abandoned, the disclosure of which is hereby incorporated herein by reference.

FIELD OF THE INVENTION

This invention relates to bis-naphthalimides, including 2,2'-[1,2-ethanediylbis(methylimino-2,1-ethanediyl)]-bis[5-nitro-1H-benz[de]isoquinoline-1,3(2H)-dione], 2-[2-[N-methyl-N-[2-[[2-(5-nitro-1,3-dioxo-1H-benz[de] isoquinoline-2(3H)-yl)ethyl]amino]ethyl]amino]ethyl]-5-nitro-1H-benz[de]isoquinoline-1,3(2H)-dione, 2,2'-[1,2-ethanediylbis(imino-2,1 -ethanediyl)]-bis[5-nitro-1H-benz[de]isoquinoline-1,3(2H)-dione], pharmaceutical compositions containing them, and methods of using them to treat solid tumor carcinomas in mammals.

BACKGROUND OF THE INVENTION

Harnisch et al., U.S. Pat. No. 4,919,848 discloses naphthalic acid imides useful as charge-regulating substances useful in electrophotographic toners.

Brana et al., U.S. Pat. No. 4,874,863 discloses anticancer compounds of the formula:

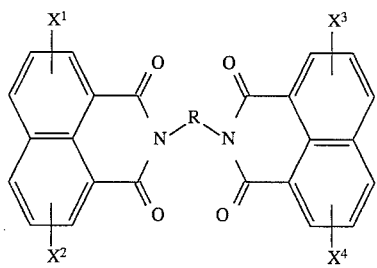

wherein $X^1$, $X^2$, $X^3$ and $X^4$ are identical or different and are each H, $NO_2$, $NH_2$, $C_1$–$C_6$-alkylamino, di-$C_1$–$C_6$-alkylamino, OH, $C_1$–$C_6$-alkoxy, halogen, trihalomethyl, $C_1$–$C_6$ alkyl, formyl, $C_1$–$C_6$-alkylcarbonyl, $C_1$–$C_6$-acylamino, ureyl, $C_1$–$C_6$-alkylureyl, or $C_1$–$C_6$-alkylcarbonylamino and R is a straight chain or branched $C_4$–$C_{10}$-alkylene which is interrupted at one or two points in the chain by a secondary or tertiary amino group, where 2 nitrogen atoms may additionally be bonded to one another by an alkylene group, or a salt with a physiologically tolerated acid.

Brana et al., U.S. Pat. No. 4,874,863 does not specifically disclose the compounds of the present invention. The compounds specifically disclosed in U.S. Pat. No. 4,874,863 are substantially less soluble than the compounds of the present invention and therefore present formulation problems when trying to formulate such compounds into a dosage form suitable for human use.

It has been found that the compounds of the present invention have dramatically increased water solubility which is an unexpected advantage over the compounds of the above identified patent.

In addition, the compounds of the present invention exhibit unexpected superior antitumor activity relative to the compounds specifically disclosed by Brana et al.

DETAILED DESCRIPTION OF THE INVENTION

There is described a compound of the formula:

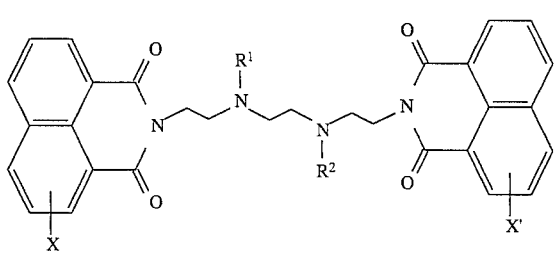

or a pharmaceutically acceptable salt thereof, wherein:
$R^1$ and $R^2$ are independently H or $CH_3$; and
X and X' are independently H, or $NO_2$, provided that at least one of X or X' is $NO_2$.

Specifically preferred compounds of the invention are:
2,2'-[1,2-ethanediylbis(methylimino-2,1-ethanediyl)]-bis[5-nitro-1H-benz[de]isoquinoline-1,3(2H)-dione];
2-[2-[N-methyl-N-[2-[[2-(5-nitro-1,3-dioxo-1H-benz[de] isoquinoline-2(3H)-yl)ethyl]amino]ethyl]amino]ethyl]-5-nitro-1H-benz[de]isoquinoline-1,3(2H)-dione;
2,2'-[1,2-ethanediylbis(imino-2,1-ethanediyl)] -bis[5-nitro-1H-benz[de]isoquinoline-1,3(2H)-dione]; and
pharmaceutically acceptable salts thereof.

Also provided by this invention are pharmaceutical compositions containing the compounds of formula (i) described above, and methods of using these compounds for the treatment of solid tumor carcinomas in a mammal.

The compounds provided by this invention are also useful as standard or reference compounds for use in tests or assays for determining the ability of an agent to inhibit human tumors xenografted in mice, for example in a pharmaceutical research program. Thus, the compounds of the present invention may be used as a control or reference compound in such assays and as a quality control standard. The compounds of the present invention may be provided in a commercial kit or container for use as such standard or reference compound.

The compounds of the present invention, although encompassed within the broad scope of U.S. Pat. No. 4,874,863, are not specifically claimed or exemplified therein. The compounds of the present invention were discovered to have significantly increased antitumor activity relative to the compounds specifically disclosed in Brana et al., U.S. Pat. No. 4,874,863. Whereas the compounds of the present invention exhibit very potent in vivo activity against solid tumors, the structurally similar compounds specifically disclosed by Brana et al. were found to be inactive.

In addition, the N-methyl substituted compounds of the present invention, such as Example 1, were found to have unexpected increased water solubility. This was unexpected since the addition of hydrophobic methyl groups to the molecule would be expected to cause a decrease in water solubility of the molecule.

Compounds of this invention can be synthesized by reacting two equivalents of an anhydride of formula (ii) with one equivalent of a polyamine of formula (iii) in an inert solvent such as ethanol or dimethylformamide or tetrahydrofuran at a temperature ranging from ambient to the solvent's boiling temperature (Scheme A, below). The resulting suspension can then be filtered to give the free base of (i) or it can be acidified with the appropriate mineral or organic acid to produce a pharmaceutically acceptable salt, which can be obtained by filtration. Salts of the free base can also be prepared by acidifying a suspension of the free base in ethyl alcohol or dichloromethane with the appropriate mineral or organic acid and collecting the formed solid by filtration. In some cases, the free base of (i) requires purification by column chromatography before its salt can be prepared as described above.

Scheme A

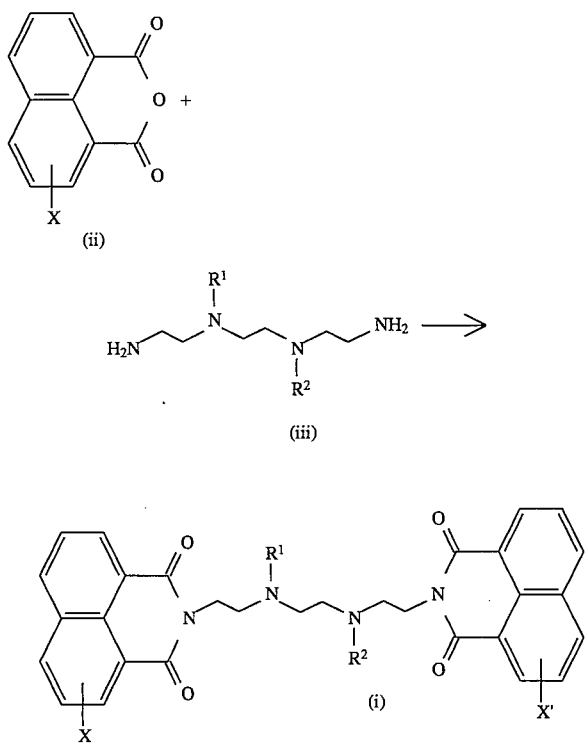

The parent anhydride (ii) is commercially available or can be prepared according to the procedures described by Hodgson et al., *J. Chem. Soc.*, p90 (1945). Compounds of formula (iii) can be prepared according to the methods described below.

EXAMPLE 1

2,2'-[1,2-Ethanediylbis(methylimino-2,1-ethanediyl)] -bis [5-nitro-1H-benz[de]isoquinoline-1,3(2H)-dione]methanesulfonate (1:2) (Ia)

The compound of Example 1 may be synthesized by the following process (see also Scheme 1 below).

Part A: Bis(1,1'-dimethylethyl)[1,2-ethanediylbis(methylimino-2-oxy-2,1-ethanediyl)]bis(carbamate) (IIa).

A methylene chloride (300 ml) solution of N-t-BOC-glycine (17.52 g, 100 mmol and 1,1'-carbonyldiimidazole (17.02 g, 105 mmol) were stirred with an ice bath cooling for two hours. To this, there was added a methylene chloride (40 ml) solution of N,N'-dimethylethylenediamine at 0°–5° C. The mixture was stirred at ambient temperature overnight. The solution was washed with saturated $Na_2CO_3$ (2×100 ml), brine (1×100 ml), dried over anhydrous $MgSO_4$, filtered and evaporated to give 18.83 g (46.8% yield) of IIa as a white solid: mp 112°–118° C. NMR ($CDCl_3$) δ5.43 (broad, 2H, 2 NH), 3.85–3.98 (m, 4H, 2 $CH_2$), 3.55 (s, 4H, 2 $CH_2$), 2.95 (m, 6H, 2 $CH_2$) and 1.44 (s, 18H, 6 $CH_3$). MS (DCI) m/e 403 (M+1).

Part B: N,N'-1,2-ethanediylbis[2-amino-N-methylacetamide]dihydrochloride (IIIa).

A mixture of IIa (12.48 g, 31.02 mmol) and 15.5 ml of 4.4N HCl in dioxane in 50 ml of dioxane at 0° C. for 3 hours, and then at room temperature for 48 hours. The mixture was warmed at 50°–55° C. for an additional 24 hours. After cooling, the mixture was added ether, and the solid collected on a filter under nitrogen to give 5.57 g (79.6%) of IIIa as a white solid, mp 223° C. (dec) NMR ($D_2O$) δ3.88, 3.80 (2 s, 4H, 2 $CH_2$), 3.45 (s, 4H, 2 $CH_2$) and 2.85 (t, 6H, 2 $CH_3$). MS (CI) m/e 203 (M+1). IR (KBr) 3435 ($NH_2$), 1665, 1649 (C=O) $cm^{-1}$.

Part C: N,N'-bis(2-aminoethyl)-N,N'-dimethyl-1,2-ethanediamine tetrahydrochloride (IVa).

To a THF (125 ml) suspension of IIIa (5.30 g, 18.32 mmol), there was added 150 ml of 1M $BH_3$.THF complex slowly. The mixture was heated to reflux overnight. Another 50 ml of 1M $BH_3$.THF complex was added, the mixture was refluxed for 24 hours. Additional 40 ml of 1M $BH_3$.THF complex was added, and the mixture was further refluxed for 72 hours. The tlc analysis ($NH_4OH$/isopropanol=1:3) indicated that the reaction was complete. The reaction solution was cooled to room temperature; and quenched with 115 ml of methanol slowly. The solution was refluxed overnight. The solvents in the solution were evaporated, and the remaining liquid was copiously added methanol (100 ml) and evaporated four times to remove trimelyl borate. The resulting viscous oil in 30 ml of methanol was added 8 ml of conc. HCl. The white solid was collected on a filter to give 3.56 g (58.2%) of IVa. NMR ($D_2O$) δ3.53 (s, 4H, 2 $CH_2$), 3.48–3.30 (m, 8H, 4 $CH_2$) and 2.83 (s, 6H, 2 $CH_3$). MS (DCI) m/e 175 (M+1).

Part D: N,N'-bis(2-aminoethyl)-N,N'-dimethyl-1,2-ethanediamine (Va).

To a freshly prepared sodium ethoxide solution (1.15 g of sodium in 60 ml of ethanol), there was added 3.56 g (11.12 mmol) of IVa. The mixture was stirred at room temperature for 2½ hours. The sodium chloride in the mixture was removed on a filter, and the solvent in the filtrate evaporated. The product in the remaining residue was purified by Kugelrohr distillation (84°–104° C. at 0.7 mm) to give 1.39 g (72%) of Va as a clear liquid. NMR ($CDCl_3$) δ2.78 (t, 4H, 2 $CH_2$), 2.50 (s, 4H, 2 $CH_2$), 2.45 (t, 4H, 2 $CH_2$) and 2.25 (s, 6H, 2 $CH_3$). MS (CDI) m/e 175 (M+1). IR(nujol) 3360, 3281 (NH, $NH_2$) $cm^{-1}$.

Part E: 2,2'-[1,2-Ethanediylbis(methylimino-2,1-ethanediyl)]-bis[5-nitro-1H-benz[de]isoquinoline-1,3(2H)-dione]methanesulfonate (1:2) (Ia).

A mixture of 3-nitro-1,8-naphthalic anhydride (1.95 g, 8.03 mmol) and Va (0.7 g, 4.02 mmol) in 30 ml of ethanol was stirred at room temperature for 24 hours. The solid was collected on a filter to give crude free base of I (2.30 g, 92% yield). This was purified by column chromatography to give pure free base, 1.27 g as a light brown solid. The free base (1.26 g, 2.0 mmol) in 40 ml of methylene chloride was added 0.39 g (4.0 mmol) of methanesulfonic acid, and the mixture stirred at room temperature overnight. The resulting precipitates were collected on a filter to give 1.76 g, which was purified by heating in methanol overnight to yield 1.18 g of Ia as a light yellow solid; mp 244°–245° C. (dec). NHR (DMSO-$d_6$) δ9.50 (d, 2H, J=1.9 Hz, aromatic protons), 9.00 (d, 2H, J=1.9 Hz, aromatic protons), 8.85 (d, 2H, J=8.0 Hz, aromatic protons), 8.74 (d, 2H, J=7.3 Hz, aromatic protons), 8.11 (t, 2H, J=7.9 Hz, aromatic protons), 4.49 (broad s, 4H, 2 CH₂), 3.37 (broad s, 8H, 4 CH₂), 2.92 (s, 6H, 2 CH₃) and 2.25 (s, 6H, 2 CH₃). MS(CI) m/e 625 (M+1). Anal. Calcd for $C_{32}H_{28}N_6O_8 \cdot 2CH_3SO_3H$ (MW 816.81): C, 50.00; H, 4.44; N, 10.29; S, 7.85. Found: C, 49.69; H, 4.33; N, 10.24; S, 7.77.

(1.0 eq) in ethanol at reflux temperature. The compound was then isolated and characterized as its methanesulfonate salt (see Scheme II).

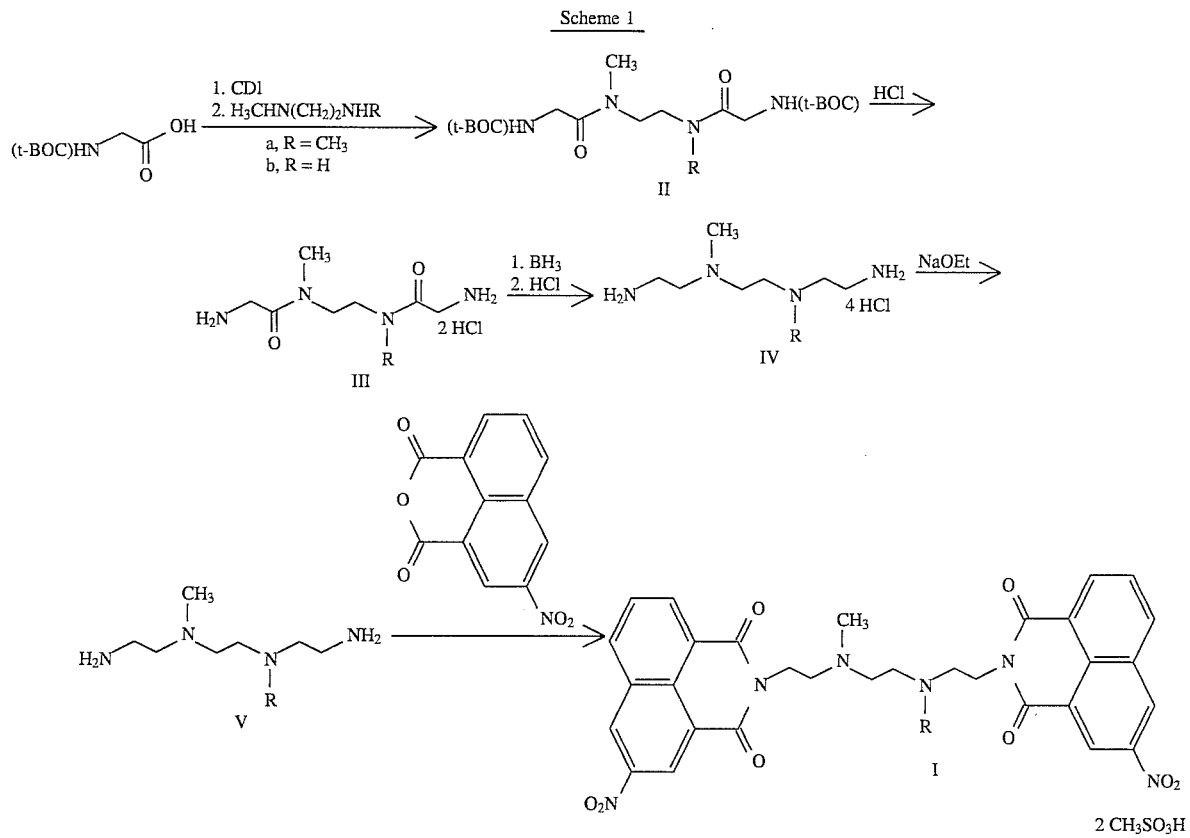

EXAMPLE 2

2-[2-[N-methyl-N-[2-[[2-(5-nitro-1,2-dioxo-1H-benz[de] isoquinoline-2(3H)-yl)ethyl]amino]ethyl]amino]ethyl]-5-nitro-1H-benz[de]isoquinoline-1,3(2H)-dione methanesulfonate (1:2) (Ib)

By replacing N,N'-dimethylethylenediamine with N-methylethylenediamine, compound Ib is prepared using the conditions described above for Example 1.

Yellow solid, mp 232°–234° C. (dec). NMR (CDCl₃) for free base δ9.28 (s, 1H, aromatic proton), 9.25 (s, 1H, aromatic proton), 9.10 (s, 2H, aromatic protons), 8.75 (t, 2H, J=7.9 Hz, aromatic protons), 8.40 (m, 2H, aromatic protons), 7.92 (m, 2H, aromatic protons), 4.52 (t, 2H, J=6.6 Hz, CH₂), 4.20 (t, 2H, J=6.4 Hz, CH₂), 2.89 (t, 2H, J=6.4 Hz, CH₂), 2.74 (s, 4H, 2 CH₂), 2.59 (t, 2H, J=5.5 Hz, CH₂) and 2.35 (s, 3H, CH₃). NMR (DMSO-d₆) for methanesulfonate salt δ9.55 (d, 2H, J=2.2 Hz, aromatic protons), 8.99 (d, 2H, J=1.1 Hz, aromatic protons), 8.84 (d, 2H, J=8.4 Hz, aromatic protons), 8.72 (d, 2H, J=7.4 Hz, aromatic protons), 8.10 (t, 2H, J=7.0 Hz, aromatic protons), 4.42 (m, 4H, 2 CH₂), 3.40 (broad, 9H, 3 CH₂ and CH₃), 2.98 (broad, 2H, CH₂) and 2.22 (s, 6H, 2 CH₃). IR (KBr) 1709, 1668 (C=O) cm⁻¹.

Anal. Calcd for $C_{31}H_{26}N_6O_8 \cdot 2CH_3SO_3H \cdot H_2O$ (MW 820.80): C, 48.29; H, 4.42, N, 10.24; S, 7.81. Found: C, 48.73, 48.73, H, 4.40, 4.39; N, 10.30, 10.27; S, 7.45, 7.40.

Compound IV can be prepared by reaction of 3-nitro-1,8-naphthalic anhydride (2.0 eq. ) and triethylenetetramine

EXAMPLE 3

2,2'-[1,2-Ethanediylbis(imino-2,1-ethanediyl)]-bis[5 -nitro-1H-benz[de]isoquinoline-1,3(2H)-dione]methanesulfonate (1:2) (VI)

A mixture of 3-nitro-1,8-naphthalic anhydride (20.0 g, 82.2 mmol) and triethylenetetramine (6.2 g, 42.4 mmol) in 900 ml of ethanol was stirred at room temperature under nitrogen for 72 hours, and then heated to reflux for 2 hours. The solid was collected on a filter to give 23.60 g of the free base (96.3% yield); mp 198°–201° C. (dec). The free base was then converted to the methanesulfonate salt as follows. To a slurry of the free base (3.0 g, 5.0 mmol) in 50 ml of methylene chloride, there was added 0.96 g (10 mmol) of methanesulfonic acid in 10 ml of methylene chloride. The mixture was then refluxed overnight. The solid was collected on a filter to give a yellow solid. This was purified by heating in 98% ethanol (200 ml) for 4 hours, filtered, and dried to give VI (see Scheme 2 below) (3.36 g, 85.2% yield) , mp 271°–273° C. (dec).

NMR (DMSO-d₆) δ9.55 (d, 2H, J=8.1 Hz, aromatic protons), 8.99 (d, 2H, J=2.5 Hz, aromatic protons), 8.84 (d, 2H, J=8.1 Hz, aromtatic protons), 8.72 (m, 2H, aromatic protons), 8.10 (t, 2H, J=7.9 Hz, aromatic protons), 4.40 (t, 4H, J=5.3 Hz, 2 CH₂), 3.40 (m, 4H, 2 CH₂), 3.31 (s, 4H, 2 CH₂) and 2.23 (s, 6H, 2 CH₃). Anal. Calcd for $C_{30}H_{24}N_6O_8 \cdot 2CH_3SO_3H$ (MW 788.76): C, 48.73; H, 4.09;

N, 10.66; S, 8.13. Found: C, 48.78; H, 3.97; N, 10.50, S, 7.92.

Scheme 2

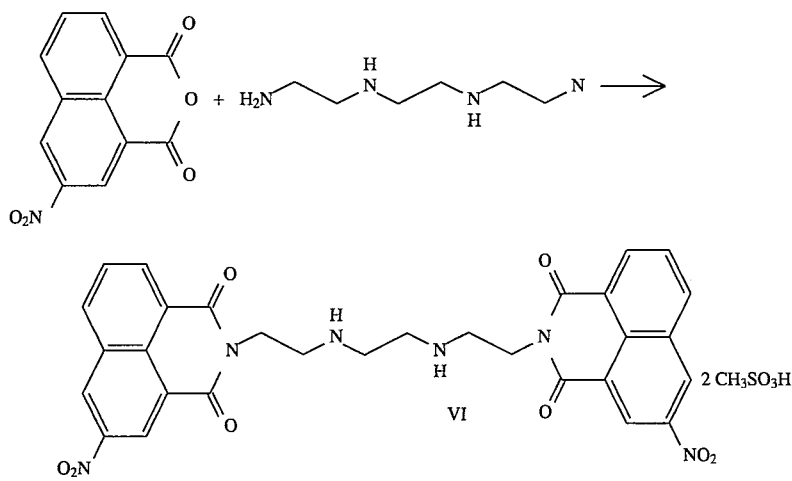

Solubility of the Compounds of the Invention

UV Method For Determining Water Solubility:

The ultraviolet spectrum is taken at room temperature of a saturated solution of the sample (saturated solution being defined as a water solution standing over excess sample for 15 to 20 hours with no heat being applied). A standard solution of the sample is obtained in water if possible. When the solubility in water is too low to do this (<1 mg/100 ml), a mg of the sample is dissolved in DMSO and diluted to 100 ml with water. Molar or gram extinction coefficients are calculated for the standard solutions and these values are used to determine the concentration of the saturated solution.

TABLE 1

| Compound | Water Solubility (g/L) | log P* |
|---|---|---|
| Ex. 1 | >26.4 | 5.02 |
| Ex. 2 | 9.6 | 4.76 |
| Ex. 3 | 0.6 | 4.50 |

*calculated partition coefficient (log P value) between octanol and water, for neutral form of the compounds.

As is evident from the data in Table 1, the compound of Example 1 has a dramatic unexpected increase in water solubility. This is unexpected due to the increase in the calculated partition coefficient (log P value) between octanol and water for the molecule.

Utility

In vitro Growth Inhibitory Activity

L1210 cells were maintained in RPMI=1640 a medium supplemented with 10% heat inactivated fetal bovine serum and 50 mL mercaptoethanol/liter medium (RPMI-L). B16 cells were maintained in RPMI-1640 medium supplemented with 15% heat inactivated fetal bovine serum and antiobiotics (RPMI-C).

Exponential growing murine leukemia L1210 cells ($1\times10^3$ cells) in 0.1 mL medium were seeded on day 0 in a 96-well microtiter plate. On day 1, 0.1 mL aliquot of medium containing graded concentrations of test analogs was added to the initial volume. After incubation at 37° C. in a humidified incubator for 3 days, the plates were centrifuged briefly and 0.1 mL of the growth medium was removed. Cell cultures were incubated with 50 µL of 3-(4, 5-dimethylthiazol-2-yl)-2,5- diphenyltetrazolium bromide (MTT; 1 mg/ml in Dulbecco's phosphate buffer saline) for 4 hours at 37° C. The resulting purple formazan precipitate was solubilized with 0.2 mL of 0.04N HCl in isopropyl alcohol. Absorbance was read in a Titertek Multiskan MCC scaning well spectrophotometer (Flow Laboratories) at a test wavelength of 570 nm and a reference wavelength of 630 nm.

The $ID_{50}$ values were determined by a computer program that fit all of the data (8 determinations per concentration and 12 concentrations per test analog) to the following equation:

$$Y=((Am-Ao)/(1+(X/ID_{50})n))+Ao$$

where: Am=absorbance of the control cells; Ao=absorbance of the cells in the presence of highest drug concentration; Y=observed absorbance; X=drug concentration; $ID_{50}$=dose of drug that inhibits the growth of cells to one half that of the control cells.

Results of the in vitro testing are shown in Table 2.

TABLE 2

| Ex. No. | $ID_{50}$ (µg/ml) |
|---|---|
| 1 | 0.0115 |
| 2 | <0.01 |
| 3 | 0.009 |

In Vivo Tumor Models

Representative compounds of the present invention have been tested in pre-clinical tests of anti-cancer activity which are indicative of clinical utility. For example, the presently claimed compounds show striking in vivo efficacy against human DLD-2 colon carcinoma xenografted in nude mice.

The methods used in the testing of compounds in the in vivo human tumor xenograft models are described below.
In Vivo Human Tumor Xenograft Models The DLD-2 human colon tumor, MX-1 human mammary carcinoma, and LX-1 human lung tumor were originally obtained from a surgically removed primary colon carcinoma, breast tumor, and non-small lung carcinoma, respectively. The human tumor lines were maintained by serial passage in athymic nude mice. The MX-1 human mammary carcinoma and LX-1 human lung tumor are established tumors used by the NCI. The DLD-2, MX-1, and LX-1 tumor models have been well characterized.

The mice used in these experiments were outbred Swiss mice or BALB/c mice bearing the nude (nu/nu) gene. On day 0 male and female mice weighing 22–30 g are inoculated with 0.2 mL of a 25% tumor mince. This mince is prepared by mincing fresh tumor tissue, grown subcutaneously in passage mice, in sterile physiological saline. Palpable tumors weighing approximately 50 mg appear in the mice within 7–10 days after inoculation. The mice are pair matched by tumor weight and sex into groups of ten each and the test compounds and vehicle control are administered intravenously (i.v.) once daily for nine consecutive days. A >20% decrease in body weight on day 5 following compound administration is considered an indication of toxicity. Tumor measurements and body weights are recorded once a week. Fifteen to 18 days after the initial injection the mice are weighed, sacrificed and the tumors excised and weighed.

The efficacy of the test compounds is determined by the extent of tumor growth inhibition in treated versus vehicle-treated control mice. Initial tumor weights (mg) are calculated from the tumor dimensions (mm) measured from caliper measurements, using the formula for a prolate ellipsoid (mg of tumor weight=(length×width$^2$)/2). Net tumor weights are calculated for each of the treated groups and the vehicle-treated control group by subtracting the initial tumor weight from the final tumor weight on day 15. Results are expressed as a percentage decrease relative to the mean tumor weight for the control vehicle-treated group.

$$\% \text{ Tumor Growth Inhibition} = \left[ 1 - \frac{\text{mean tumor weight of treated}}{\text{mean tumor weight of control}} \right] \times 100$$

Activity Criteria

The criteria of the National Cancer Institute (NCI) for activity in the in vivo cancer models were used. Tumor growth inhibition of 58–89% in the DLD-2 assay is considered moderate activity and inhibition of ≧90% is considered good to excellent activity. Actual tumor regressions (IR= incomplete regression; FR=full regression) indicate excellent to outstanding activity. Compounds demonstrating <58% growth inhibition are considered inactive.

The compounds of Examples 1, 2, and 3 exhibited excellent to outstanding activity against DLD-2 human colon tumor in vivo. The compound of Example 1 exhibited good to excellent activity against the MX-1 human breast tumor in vivo and Example 3 exhibited excellent to outstanding activity against MX-1 human breast tumor in vivo. In addition, Example 3 exhibited moderate activity against LX-1 human lung tumor in vivo.

The results described above demonstrate that the compounds of the present invention have potent effectiveness against human colon and breast tumors xenografted in mice, including high levels of tumor growth inhibition and significant levels of tumor regressions. The compounds of the present invention also exhibit potent tumor inhibiting activity against the LX-1 tumor xenograft, a tumor which is particularly refractory to antitumor agents. Based on the exceptional level of antitumor activity of the present compounds in these human tumor xenograft models, it is predicted that the compounds of the present invention will exhibit clinical effectiveness for the treatment of solid tumors, in particular, the treatment of human colon and breast tumors. This conclusion is supported by published analyses correlating pre-clinical human tumor xenograft test results with clinical efficacy of anti-cancer agents, such as Mattern et al. (1988) Cancer and Metastasis Review 7: 263–284.

The demonstrated effectiveness of the compounds of the present invention in the human colon tumor xenograft models indicate that the compounds of the present invention may be useful for the treatment of solid tumor carcinomas in man, and, in particular, tumors of the colon. The high level of in vivo antitumor activity against human colon tumors exhibited by the presently claimed compounds provide strong evidence that the compounds claimed in present invention may have important therapeutic utility in the treatment of cancer in man.

The demonstrated effectiveness of the compounds of the present invention in the human colon tumor xenograft models also demonstrates that the compounds provided by this invention are also useful as standard or reference compounds for use in tests or assays for determining the ability of an agent to inhibit human tumors xenografted in mice, for example for use in a pharmaceutical research program. Thus, the compounds of the present invention may be used as a control or reference compound in such assays and as a quality control standard. The compounds of the present invention may be provided in a commercial kit or container for use as such standard or reference compound.

Dosage and Formulation

The antitumor compounds (active ingredients) of this invention can be administered to inhibit tumors by any means that produces contact of the active ingredient with the agent's site of action in the body of a mammal. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

The dosage administered will be a tumor-inhibiting amount of active ingredient and will, of course, vary depending upon known factors such as the pharmacodynamic characteristics of the particular active ingredient, and its mode and route of administration; age, health, and weight of the recipient; nature and extent of symptoms; kind of concurrent treatment, frequency of treatment, and the effect desired. Usually a daily dosage of active ingredient can be about 5 to 400 milligrams per kilogram of body weight. Ordinarily, 10 to 200, and preferably 10 to 50, milligrams per kilogram per day given in divided doses 2 to 4 times a day or in sustained release form is effective to obtain desired results.

Dosage forms (compositions) suitable for internal administration contain from about 1.0 milligram to about 500 milligrams of active ingredient per unit. In these pharmaceutical compositions, the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Useful pharmaceutical dosage forms for administration of the compounds of this invention can be illustrated as follows.

Capsules: are prepared by filling standard two-piece hard gelatin capsules each with 100 milligrams of powdered active ingredient, 175 milligrams of lactose, 24 milligrams of talc, and 6 milligrams magnesium stearate.

Soft Gelatin Capsules: A mixture of active ingredient in soybean oil is prepared and injected by means of a positive displacement pump into gelatin to form soft gelatin capsules containing 100 milligrams of the active ingredient. The capsules are washed and dried.

Tablets: are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose. 11 milligrams of cornstrach and 98.8 milligrams of lactose. Appropriate coatings may be applied to increase palatability or delay absorption.

Injectable: A parenteral composition suitable for administration by injection is prepared by stirring 1.5% by weight of active ingredient in 10% by volume propylene glycol and water. The solution is made isotonic with sodium chloride and sterilized.

Suspension: An aqueous suspension is prepared for oral administration so that each 5 milliliters contain 100 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

In the present disclosure it should be understood that the specified materials and conditions are important in practicing the invention but that unspecified materials and conditions are not excluded so long as they do not prevent the benefits of the invention from being realized.

What is claimed is:

1. A compound which is 2,2'-[1,2-ethanediylbis(methylimino-2,1-ethanediyl)-] -bis[5-nitro-1H-benz[de]isoquinoline-1,3(2H)-dione], and pharmaceutically acceptable salts thereof.

2. A compound which is 2-[2-[N-methyl-N-[2-[[2-(5-nitro-1H-benz[de]isoquinoline-2(3H)-yl)ethyl]amino]ethyl]amino]ethyl]-5-nitro-1H-benz[de]isoquinoline-1,3(2H)-dione, and pharmaceutically acceptable salts thereof.

3. 2,2'-[1,2-ethanediylbis(imino-2,1-ethanediyl)]-bis[5-nitro-1H-benz[de]isoquinoline-1,3(2H)-dione], and pharmaceutically acceptable salts thereof.

* * * * *